(12) United States Patent
Chen et al.

(10) Patent No.: US 12,178,808 B2
(45) Date of Patent: Dec. 31, 2024

(54) AMORPHOUS SOLID DISPERSION COMPRISING 6-(1-ACRYLOYLPIPERIDIN-4-YL)-2-(4-PHENOXYPHENYL)NICOTINAMIDE

(71) Applicant: BEIJING INNOCARE PHARMA TECH CO., LTD., Beijing (CN)

(72) Inventors: Xiangyang Chen, Beijing (CN); Zuopeng Wang, Shanghai (CN); Liqin Yu, Nanjing (CN)

(73) Assignee: Beijing InnoCare Pharma Tech Co., Ltd., Beijing (CN)

( * ) Notice: Subject to any disclaimer, the term of this patent is extended or adjusted under 35 U.S.C. 154(b) by 860 days.

(21) Appl. No.: 17/241,906

(22) Filed: Apr. 27, 2021

(65) Prior Publication Data

US 2021/0260050 A1    Aug. 26, 2021

Related U.S. Application Data

(63) Continuation of application No. PCT/CN2019/113636, filed on Oct. 28, 2019.

(60) Provisional application No. 62/756,464, filed on Nov. 6, 2018.

(51) Int. Cl.
*A61K 31/4545* (2006.01)
*A61K 9/16* (2006.01)

(52) U.S. Cl.
CPC ........ *A61K 31/4545* (2013.01); *A61K 9/1635* (2013.01); *A61K 9/1652* (2013.01); *A61K 9/1694* (2013.01)

(58) Field of Classification Search
CPC .......................... A61K 31/4545; A61K 9/1635
See application file for complete search history.

(56) References Cited

U.S. PATENT DOCUMENTS

| | | |
|---|---|---|
| 2012/0328679 A1 | 12/2012 | Curatolo et al. |
| 2018/0193274 A1 | 7/2018 | Nunn et al. |

FOREIGN PATENT DOCUMENTS

| | | |
|---|---|---|
| CN | 105816423 A | 8/2016 |
| CN | 106999494 A | 8/2017 |
| CN | 107308133 A | 11/2017 |
| EP | 3431075 A1 | 1/2019 |
| WO | 2013105894 A1 | 7/2013 |
| WO | 2015048662 A2 | 4/2015 |
| WO | 2016019233 A1 | 2/2016 |
| WO | 2016100914 A1 | 6/2016 |
| WO | WO2016105582 A1 * | 6/2016 |
| WO | 2018/007556 A1 | 1/2018 |

OTHER PUBLICATIONS

Fang Liang "Solid Dispersion" Pharmacy China Medical Science Press, Mar. 31, 2016. pp. 85-87 with English translation.
International Search Report for PCT Application No. PCT/CN2019/113636. Mail Date: Feb. 3, 2020. 5 pages.
Van den Mooter "The use of amorphous solid dispersions: A formulation strategy to overcome poor solubility and dissolution rate" Drug Discovery Today: Technologies, vol. 9, Issue 2, Summer 2012, pp. e79-e85.
Newman, et al. "Assessing the Performance of Amorphous Solid Dispersions" Published online Dec. 27, 2011 in Wiley Online Library (wileyonlinelibrary.com). DOI 10.1002/jps.23031, 23 pages.
Extended European Search Report mailed May 20, 2022 for European Application No. 19881429.5. 3 pages.

* cited by examiner

*Primary Examiner* — Kamal A Saeed
*Assistant Examiner* — Karen Cheng
(74) *Attorney, Agent, or Firm* — Viola Kung; Perkins Coie LLP

(57) ABSTRACT

The present invention relates to an amorphous solid dispersion comprises 6-(1-acryloylpiperidin-4-yl)-2-(4-phenoxyphenyl)nicotinamide (Compound I) or a pharmaceutically acceptable salt thereof, and a pharmaceutically acceptable polymer. The present invention also relates to pharmaceutical compositions comprising the amorphous solid dispersion. The amorphous solid dispersion of the present invention is stable upon storage and provides a better dissolution rate and bioavailability when comparing with a crystalline form.

6 Claims, 5 Drawing Sheets

AMORPHOUS SOLID DISPERSION COMPRISING 6-(1-ACRYLOYLPIPERIDIN-4-YL)-2-(4-PHENOXYPHENYL)NICOTINAMIDE

This application is a continuation of PCT/CN2019/113636, filed Oct. 28, 2019; which claims the benefit of U.S. Provisional Application No. 62/756,464, filed Nov. 6, 2018. The contents of the above-identified applications are incorporated herein by reference in their entirety.

TECHNICAL FIELD

The present invention relates to amorphous solid dispersions of 6-(1-acryloylpiperidin-4-yl)-2-(4-phenoxyphenyl)nicotinamide.

BACKGROUND OF THE INVENTION 6-(1-Acryloylpiperidin-4-yl)-2-(4-phenoxyphenyl)nicotinamide (Compound I) is a substituted nicotinamide inhibitor of Bruton's Tyrosine Kinase (BTK). The preparation of Compound I and its use in the treatment of cancer, inflammation, and autoimmune disease is described in WO2015/028662, which is incorporated herein by reference in its entirety.

DETAILED DESCRIPTION OF THE INVENTION

Figure 1:
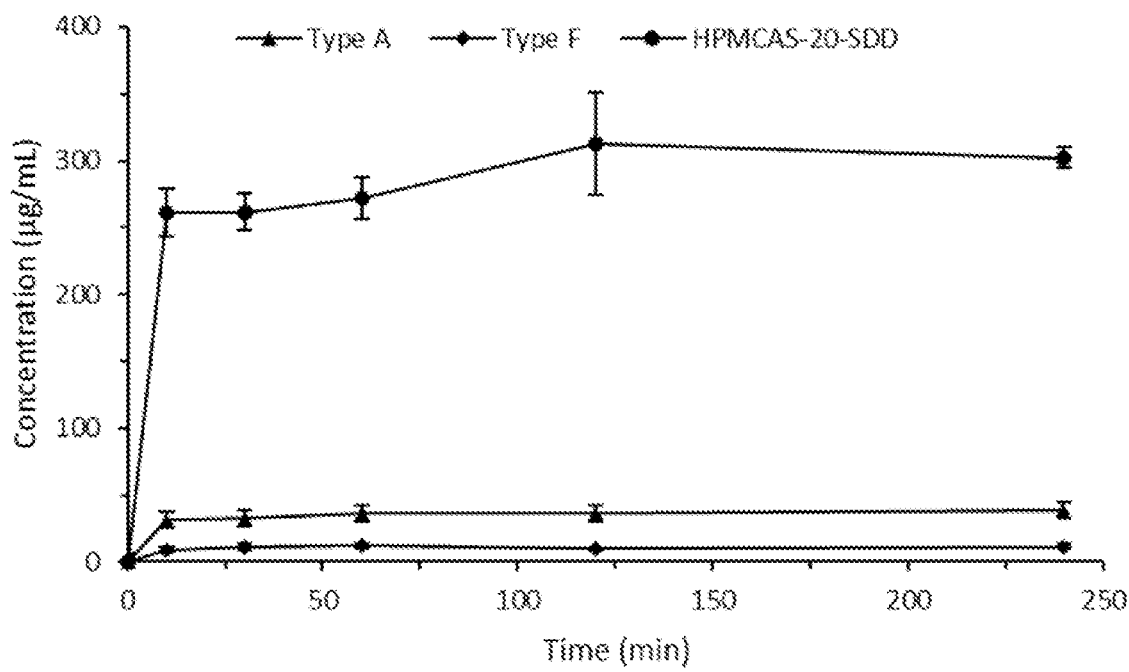
FIG. 1 shows the dissolution behaviors of Type A crystal, Type F crystal, and HPMCAS-20-SDD (ASD with 20% drug loading made via spray-drying dispersion).

The present invention is directed to an amorphous solid dispersion (ASD) form comprising 6-(1-acryloylpiperidin-4-yl)-2-(4-phenoxyphenyl)nicotinamide (Compound I), or a pharmaceutically acceptable salt thereof, and a pharmaceutically acceptable polymer.

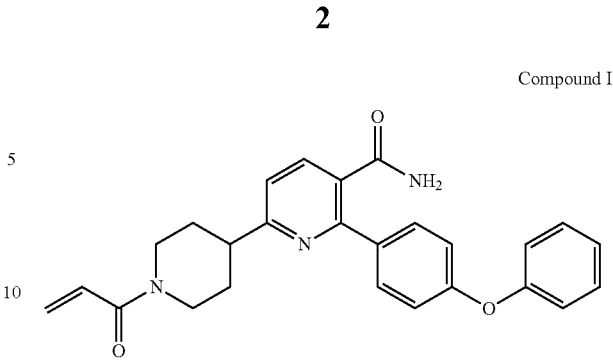

Compound I

The inventors have discovered that the ASD form of Compound I has advantages over the crystalline form for use in preparing a drug formulation. The ASD form of Compound I has good bioavailability, good solubility, good dissolution, and is chemically and physically stable.

Type A Crystalline Form

Type A crystalline form is prepared from a starting material Compound I, as described in WO2015/048662. Type A crystalline form can be prepared by dissolving the starting material Compound I in dichloromethane; then precipitating with ethyl acetate.

The X-ray powder diffraction (XRPD) data of Type A is shown in Table 1.

TABLE 1

| 2theta | d spacing | Intensity (%) |
|---|---|---|
| 5.39 | 16.41 | 100.00 |
| 8.41 | 10.51 | 77.19 |
| 10.11 | 8.75 | 19.53 |
| 11.06 | 8.00 | 15.79 |
| 13.23 | 6.69 | 17.33 |
| 13.64 | 6.49 | 4.27 |
| 14.29 | 6.20 | 9.80 |
| 16.08 | 5.51 | 27.72 |
| 16.35 | 5.42 | 21.31 |
| 17.71 | 5.01 | 13.12 |
| 18.69 | 4.75 | 64.74 |
| 19.14 | 4.64 | 43.60 |
| 21.02 | 4.23 | 16.01 |
| 21.85 | 4.07 | 22.24 |
| 23.25 | 3.83 | 8.69 |
| 23.61 | 3.77 | 7.55 |
| 25.25 | 3.53 | 5.99 |
| 26.82 | 3.32 | 4.31 |
| 29.59 | 3.02 | 3.00 |

Type A of present disclosure shows a solubility of 0.013 mg/mL after equilibrium in water at room temperature for 24 hours.

Type F Crystalline Form

Type F can be prepared from Type A via slurry in a solvent or a solvent mixture (e.g., methanol, ethanol, acetonitrile, methanol/water, or ethanol/water).

The XRPD data of Type F is shown in Table 2.

TABLE 2

| 2theta | d spacing | Intensity |
|---|---|---|
| 6.18 | 14.30 | 47.96 |
| 11.20 | 7.90 | 6.61 |
| 11.85 | 7.47 | 33.51 |
| 12.38 | 7.15 | 77.36 |
| 12.88 | 6.87 | 3.98 |
| 13.43 | 6.59 | 16.62 |
| 14.25 | 6.22 | 20.00 |

TABLE 2-continued

| 2theta | d spacing | Intensity |
|---|---|---|
| 14.64 | 6.05 | 11.77 |
| 15.03 | 5.89 | 6.50 |
| 16.05 | 5.52 | 15.91 |
| 17.89 | 4.96 | 30.09 |
| 18.75 | 4.73 | 100.00 |
| 18.96 | 4.68 | 35.16 |
| 19.48 | 4.56 | 7.84 |
| 19.75 | 4.50 | 15.42 |
| 20.12 | 4.41 | 43.61 |
| 21.16 | 4.20 | 6.47 |
| 21.52 | 4.13 | 7.51 |
| 21.81 | 4.07 | 9.82 |
| 22.03 | 4.04 | 15.23 |
| 22.81 | 3.90 | 47.92 |
| 23.61 | 3.77 | 20.50 |
| 23.86 | 3.73 | 20.57 |
| 24.74 | 3.60 | 6.37 |
| 25.94 | 3.43 | 4.67 |
| 26.38 | 3.38 | 3.62 |
| 26.87 | 3.32 | 13.70 |
| 27.22 | 3.28 | 5.36 |
| 27.65 | 3.23 | 11.63 |
| 29.22 | 3.06 | 4.23 |
| 29.66 | 3.01 | 6.86 |
| 31.28 | 2.86 | 8.51 |
| 32.54 | 2.75 | 2.45 |
| 34.24 | 2.62 | 0.99 |
| 35.03 | 2.56 | 1.43 |
| 37.95 | 2.37 | 2.10 |

Type F is an anhydrate.

Type F of present disclosure shows a solubility of 0.004 mg/mL after equilibrium in water at room temperature for 24 hours.

Type F is a stable crystalline form and is useful as an active pharmaceutical ingredient (API) for a pharmaceutical formulation. However, its dissolution is slow and bioavailability is low (20%).

Amorphous Solid Dispersion (ASD)

The ASD form of Compound I comprises Compound I or a pharmaceutically acceptable salt thereof, and a pharmaceutically acceptable polymer. The ASD form of Compound I is stable in an amorphous form in a solid state for extended periods of time that may be used for preparing a drug formulation. The ASD form of Compound I has a desirable pharmaceutical profile, and it is amenable to manufacturing conditions.

The pharmaceutically acceptable salts of Compound I suitable for use in ASD of the present invention are conventional non-toxic salts and can include an inorganic acid addition salt (e.g., hydrochloride, hydrobromide, sulfate, phosphate, etc.); an organic carboxylic or sulfonic acid addition salt (e.g., formate, acetate, trifluoroacetate, maleate, tartrate, methanesulfonate, benzenesulfonate, p-toluenesulfonate, etc.), or a salt with an acidic amino acid such as aspartic acid, glutamic acid, etc.).

A pharmaceutically acceptable polymer is included in ASD to stabilize the compound and the dispersion, which may be a hydrophilic carrier polymer, which may include cellulose based polymers (e.g., hydroxypropylmethyl cellulose (HPMC, hypromellose), ethyl cellulose, hydroxyethyl cellulose, hydroxyethylmethyl cellulose, hydroxypropyl cellulose, hypromellose phthalate (HPMCP), cellulose acetate, cellulose acetate phthalate, methylcellulose, ethylcellulose, cellulose, carboxymethylcellulose, microcrystalline cellulose, silicified microcrystalline cellulose, etc.), starch based polymers (e.g., hydroxypropyl starch, starches (including starches from any source, such as corn, potato, rice, wheat, which can be fully pregelatinized and partially gelatinized)), polyethylene glycol, polyacrylic acid, polyacrylamide, polyethylene oxide, polyvinylpyrrolidone, polyvinylalcohol, polyglycolized glycerides, polymethacrylates, hydrocolloids (e.g., carrageenan, chitosan, alginic acid, hyaluronic acid, pectinic acid, etc.).

Preferred polymers for the present invention include hydroxypropylmethylcellulose-acetate succinate (HPMC-AS), polyvinylpyrrolidone-vinyl acetate copolymer (PVP-VA), polyvinylpyrrolidone (PVP), and hydroxypropylmethylcellulose (HPMC). HPMC-AS and PVP-VA are further preferred.

The amount of Compound I in ASD is in general 10-60%, or 10-50%, 10-40%, 15-50%, or 15-45% by weight. For example, the amount of Compound I in ASD (drug loading) is 20% or 40% by weight.

The weight ratio of Compound I to the pharmaceutically acceptable polymer (e.g., HPMC-AS or PVP-VA) is in general in the range of 1:1 to 1:10, or 1:1 to 1:4.

For example, the ASD form of Compound I comprises 20-40% w/w of Compound I and 60-80% w/w of HPMC-AS.

For example, the ASD form of Compound I comprises 20-40% w/w of Compound I and 60-80% w/w of PVP-VA.

In one preferred embodiment, the ASD of the present invention does not include any surfactant.

In another embodiment, the ASD of the present invention may include a surfactant to enhance solubility and/or to improve physical stability. A surfactant in general is in an amount of 5-40% w/w, preferably 10-30% w/w of the ASD. A pharmaceutically acceptable surfactant useful as an additive in the solid dispersion may include polysorbate (e.g., polysorbate 20, polysorbate 40, polysorbate 80, polysorbate 85, polysorbate 60, etc.), cyclodextrin, polyoxyl 20 stearate, polyoxyl 35 castor oil, poloxamer, polyoxyethylene sorbitan monoisostearate, polyethylene glycol 40 sorbitan diisostearate, polyoxyl 40 hydrogenated castor oil, poloxamer 331, polyoxyethylene fatty acid esters, polyoxyl 40 castor oil, poloxamer 188, polyoxyethylene polyoxypropylene 1800, oleic acid, sodium desoxycholate, sodium lauryl sulfate, sorbitan monolaurate, sorbitan monooleate, sorbitan monopalmitate, sorbitan trioleate, N-carbamoyl methoxy-polyethylene glycol 2000-1,2-distearol, myristic acid, steareth, stearic acid, polyoxyl 40 stearate, polyoxyl 60 stearate, sucrose stearate, tocopherol, polyoxyl castor oil, triglyceride synthetic, trimyristin, tristearin, magnesium stearate, lecithin, lauryl sulfate, vitamin E, egg yolk phosphatides, docusate sodium, dimyristoyl phosphatidylglycerol, dimyristoyl lecithin, Capryol 90 (propylene glycol monocaprylate), Capryol PGMC (propylene glycol monocaprylate), deoxycholate, cholesterol, Cremophor EL, Propylene glycol alginate, Croval A-10 (PEG 60 almond glycerides), Labrafil 1944 (oleoyl macrogol-6 glycerides), Labrafil 2125 (linoleoyl macrogol-6 glycerides), Labrasol (caprylocaproyl macrogol-8 glycerides), Lauroglycol 90 (propylene glycol monolaurate), Lauroglycol FCC (propylene glycol laurate), calcium stearate, Lecithin Centromix E, Lecithin Centrophase 152, Lecithin Centrol 3F21B, POE 26 glycerin, Olepal isosteariques (PEG-6 isostearate), Plurol diisostearique (polyglycerol-3-diisostearate), Plurol Oleique CC, POE 20 Sorbitan trioleate, Tagat TO (polyoxyethylene glycerol trioleate), or Solutol (Macrogol-15 hydroxystearate), or a mixture thereof. Preferred surfactants are polysorbate and β-cyclodextrin.

The thermochemical properties of the ASD is analyzed with a differential scanning calorimeter (DSC). The results show that ASD of Compound I only has one glass transition temperature and does not show any endothermic peak (melting peak), which confirms that Compound I being amorphous in ASD. The resulting ASD can be formulated into pharmaceutical compositions that exhibit high bioavailability.

The ASD of the present invention provides a better dissolution rate when dissolved in fasted-state simulated intestinal fluid than Type A crystalline, which in turn is better than Type F crystalline.

The ASD of the present invention is stable and remains as amorphous for at least one week at 25-40° C. in 60-75% relative humidity.

In one embodiment, the ASD of the present invention is chemically stable and exhibits less than about 5% degradation when stored at 25° C. in 60% for at least one years.

Method for Preparing ASD

The ASD of the present invention may be prepared by spray drying, hot melt extrusion, or lyophilization technique.

The solid matrix has Compound I finely dispersed (molecular dispersion) in such a way that the dissolution of the compound is maximized, thus improving the bioavailability of the compound.

In one embodiment, the ASD of the present invention is prepared by dissolving Compound I in a sufficient amount of an organic solvent, and mixing the resultant solution with a solution containing a pharmaceutically acceptable polymer and optionally a solubility enhancer such as a surfactant, thereby preparing a spray solution. The solvent may then be evaporated away, leaving the drug dispersed/dissolved in the matrix.

In one embodiment, the method comprises the steps of: (a) dissolving Compound I or a pharmaceutically acceptable salt thereof, and a pharmaceutically acceptable polymer in a solvent; and (b) drying the solution obtained in step (a).

In one embodiment, step (a) comprises: dissolving Compound I in a sufficient amount of an organic solvent; dissolving a pharmaceutically acceptable polymer in a solvent; and mixing the two solutions.

In one embodiment, organic solvents are used for dissolving Compound I and the polymer. The organic solvents may include an alcohol, a haloalkane, acetone, acetic acid, ethyl acetate, N,N-dimethylformamide, DMSO, tetrahydrofuran, or a mixture thereof. For example, the alcohol is methanol, ethanol, propanol or isoprapanol. For example, the haloalkane is dichloromethane, chloroform or carbon tetrachloride.

In one embodiment, water or a mixture of water and an organic solvent is sued for dissolving Compound I and the polymer.

In one embodiment, step (b) comprises spray drying. In another embodiment, step (b) comprises spray drying in combination with a fluid bed. In a further embodiment, step (b) comprises evaporation of the solvent using a rotovap.

In one embodiment, the solvent may be removed by evaporation by spray drying technique. The term "spray drying" is used conventionally and broadly refers to processes involving breaking up liquid mixtures into small droplets (atomization) and rapidly removing solvent from the mixture in a spray-drying apparatus (e.g., a nozzle) where there is a strong driving force for evaporation of solvent from the droplets. In a typical spray drying process, the feed liquid may be a solution, slurry, emulsion, gel or paste, provided it is pumpable and capable of being atomized.

Spray-drying processes and spray-drying equipment are described generally in Perry's Chemical Engineers' Handbook, pages 20-54 to 20-57 (Sixth Edition 1984). The driving force for solvent elimination or evaporation is usually provided by keeping the partial pressure of solvent in the spray-drying equipment substantially below the vapor pressure of the solvent at the temperature of the drying droplets.

Once the spraying is over, the feed and atomization are stopped, and the resultant solid dispersion is collected and dried further if necessary in an oven at about 40-60° C.

In one embodiment, ASD is prepared by hot-melt extrusion. In this method, Compound I and a polymer are first mixed uniformly. The mixture is fed to an extruder and extruded at a high temperature over 100° C. The collected solid is grinded and passed through a mesh filter to produce ASD powder.

Pharmaceutical Composition

The present invention is also directed to a pharmaceutical composition comprising a therapeutically effective amount of Compound I in ASD form, and a pharmaceutically acceptable carrier in a solid form.

Pharmaceutically acceptable carriers, which are inactive ingredients, can be selected by those skilled in the art using conventional criteria. Pharmaceutically acceptable carriers include, but are not limited to, non-aqueous based solutions, suspensions, emulsions, microemulsions, micellar solutions, gels, and ointments. The pharmaceutically acceptable carriers may also contain ingredients that include, but are not limited to, saline and aqueous electrolyte solutions; ionic and nonionic osmotic agents such as sodium chloride, potassium chloride, glycerol, and dextrose; pH adjusters and buffers such as salts of hydroxide, phosphate, citrate, acetate, borate, and trolamine; antioxidants such as salts, acids and/or bases of bisulfite, sulfite, metabisulfite, thiosulfite, ascorbic acid, acetyl cysteine, cystein, glutathione, butylated hydroxyanisole, butylated hydroxytoluene, tocopherols, and ascorbyl palmitate; surfactants such as lecithin, phospholipids, including but not limited to phosphatidylcholine, phosphatidylethanolamine and phosphatidyl inositol; poloxamers and ploxamines, polysorbates such as polysorbate 80, polysorbate 60, and polysorbate 20, polyethers such as polyethylene glycols and polypropylene glycols; polyvinyls such as polyvinyl alcohol and povidone; cellulose derivatives such as methylcellulose, hydroxypropyl cellulose, hydroxyethyl cellulose, carboxymethyl cellulose and hydroxypropyl methylcellulose and their salts; petroleum derivatives such as mineral oil and white petrolatum; fats such as lanolin, peanut oil, palm oil, soybean oil; mono-, di-, and triglycerides; polymers of acrylic acid such as carboxypolymethylene gel, and hydrophobically modified cross-linked acrylate copolymer; polysaccharides such as dextrans and glycosaminoglycans such as sodium hyaluronate. Such pharmaceutically acceptable carriers may be preserved against bacterial contamination using well-known preservatives, these include, but are not limited to, benzalkonium chloride, ethylene diamine tetra-acetic acid and its salts, benzethonium chloride, chlorhexidine, chlorobutanol, methylparaben, thimerosal, and phenylethyl alcohol, or may be formulated as a non-preserved formulation for either single or multiple use.

For example, a tablet formulation or a capsule formulation comprising Compound I may contain other excipients that have no bioactivity and no reaction with the active compound. Excipients of a tablet may include fillers, binders, lubricants and glidants, disintegrators, wetting agents, and release rate modifiers. Binders promote the adhesion of particles of the formulation and are important for a tablet formulation. Examples of binders include, but are not limited to, carboxymethylcellulose, cellulose, ethylcellulose, hydroxypropylmethylcellulose, methylcellulose, karaya gum, starch, and tragacanth gum, poly(acrylic acid), and polyvinylpyrrolidone.

In a further embodiment the composition is tableted.

In one embodiment, a tablet formulation comprises ASD of the present invention in a weight range of 10-75%, preferably 20-60% or 45-55%.

In one embodiment, a tablet formulation comprises one or more fillers, for example lactose and/or microcrystalline cellulose, in a total weight percent range of 10-80%, preferably 20-70% or 30-60%.

In one embodiment, a tablet formulation comprises a disintegrant in a weight percentage of 4-10%, preferably 4-9%, and more preferably 5-7%.

In one embodiment, a tablet formulation comprises a lubricant, for example magnesium stearate, in a weight percent range of 0.25-2.0%, preferably 0.25-1.0%, and more preferably 0.25-0.75%.

The following examples further illustrate the present invention. These examples are intended merely to be illustrative of the present invention and are not to be construed as being limiting.

EXAMPLES

Example 1. Preparation of Type A

The starting material Compound I was prepared according to the procedures described in Example 3 of WO2015/048662. The starting material Compound I was dissolved in dichloromethane and ethyl acetate was then added dropwise with stirring until solid was precipitated out. The solid was isolated by filtration and washed with ethyl acetate to give Type A crystalline form.

Example 2. Preparation of Type F 100.1 mg of Type A was added into 2.5 mL of acetonitrile and the resulting mixture was stirred at room temperature for 20 days. Type F was obtained after centrifugation and drying.

Example 3. Preparation of ASD by Spray Drying Dispersion (20% Drug Loading)

2.02 g of Compound I was dissolved in 270 mL of methanol at room temperature. While stirring at 100 rpm, 8.00 g of HPMC-AS (AS-MF) was added slowly. After addition, stirring was continued for 3-4 h until a clear solution was obtained. The solution was then placed in a Yamato ADL 311SA spray-dryer for ASD preparation which was set with inlet temperature of 80° C., outlet temperature of 50-54° C., flow-rate of 7-8 mL/min and spray air pressure of 0.1 MPa. The collected spray-dried material was transferred to a glass dish, covered and vacuum-dried overnight to give 5.64 g ASD powder.

Example 4. Preparation of ASD by Hot Melt Extrusion (20% Drug Loading)

2.40 g of Compound I and 9.60 g of PVP-VA were mixed uniformly. After passing through a 40-mesh filter, the mixture was fed to a Thermo MiniCTW extruder for ASD preparation under temperature of 150-160° C. and speed of 30 rpm. The collected yellow solid was grinded and passed through a 40-mesh filter to give 5.50 g ASD powder.

Example 5. Dissolution Behaviors of Type A, Type F and ASD 10 mg of accurately weighted samples of Type A and Type F, and 50 mg of HPMCAS-20-SDD (ASD with 20% drug loading made via spray-drying dispersion, see Example 3) were each added to 20 mL of fasted-state simulated intestinal fluid (FaSSIF) solution (pH 6.5) in a 50-mL centrifuge tube. The tube was placed in a shaker and kept shaking with 100 rpm at 37° C. At different time intervals (10, 30, 60, 120, 240 min), 350 µL suspension was removed and centrifuged at 13,000 rpm for 3 minutes to give a clear solution that was then analyzed by HPLC. The results (averaged from three repeats) are shown in FIG. 1. The results show that ASD's dissolution in FaSSIF is much better than that of Type A, which in turn is better than Type F's.

Example 6. Glass Transition Temperature

Accurately weighted samples (containing 5 mg of Compound I. see Table 3) were prepared according to the protocols of Examples 3 and 4, except varying the polymer and the drug amount. The examples were each placed in a DSC pan (TA Instruments), which was then sealed and placed in a TA Instruments Q2000. The pan was heated at 105° C. for 3 minutes and then rapidly cooled to 0° C. for 1 minute. The DSC analysis was carried out between 0 to 180° C. at a rate of 10° C./min. The glass transition temperatures (Tg) are summarized in Table 3.

TABLE 3

| Sample | Polymer | ASD Preparation Method | Drug Loading (%) | Tg (° C.) |
|---|---|---|---|---|
| Type A | None | | 100 | 69.4 |
| HPMCAS-20-SDD | HPMC-AS | Spray Drying Dispersion | 20 | 83.5 |
| HPMCAS-40-SDD | HPMC-AS | Spray Drying Dispersion | 40 | 72.6 |
| HPMCAS-60-SDD | HPMC-AS | Spray Drying Dispersion | 60 | 69.6 |
| PVPVA-20-HME | PVP-VA | Hot Melt Extrusion | 20 | 96.4 |
| PVPVA-40-HME | PVP-VA | Hot Melt Extrusion | 40 | 86.6 |
| PVPVA-50-HME | PVP-VA | Hot Melt Extrusion | 60 | 86.5 |

DSC curves showed that there was only one glass transition temperature without observed melting peak, indicating that Compound I existed in amorphous state among polymers made by both techniques. When the percentage of drug loading increased from 20% to 60%, Tg decreased, therefore the risk of phase separation increased. It would be desirable to keep drug loading low to ensure physical stability.

Figure 2:
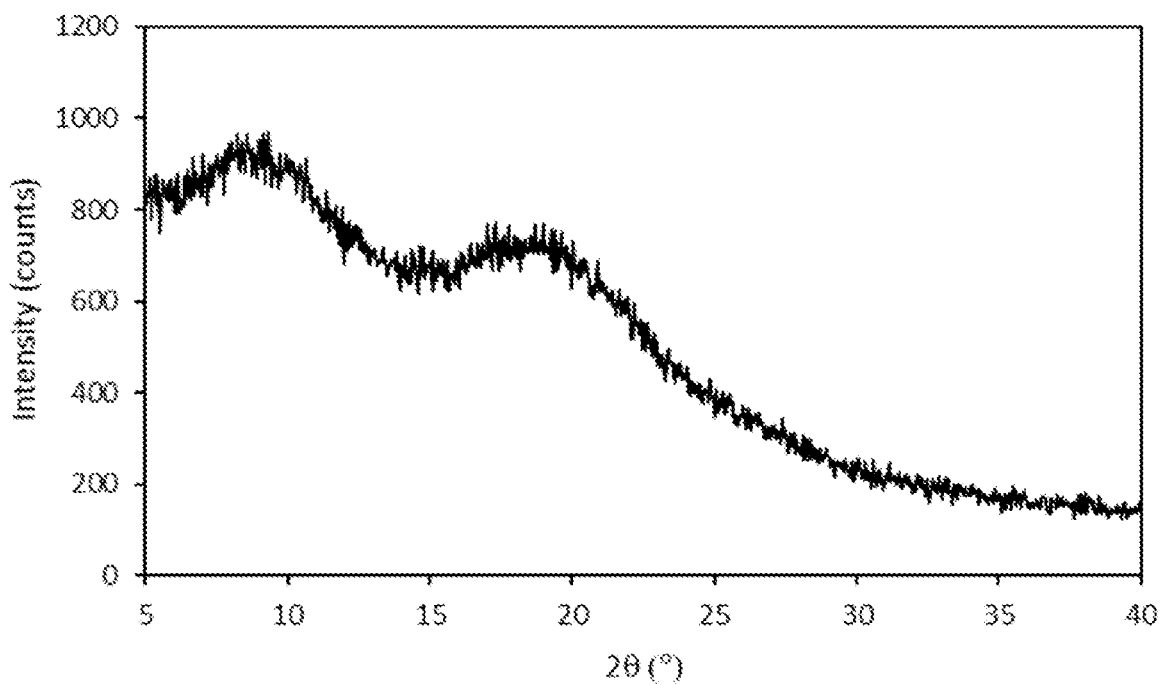
FIG. 2 shows the XRPD of HPMCAS-20-SDD.

The XRPD of HPMCAS-20-SDD is shown in FIG. 2.

Figure 3:
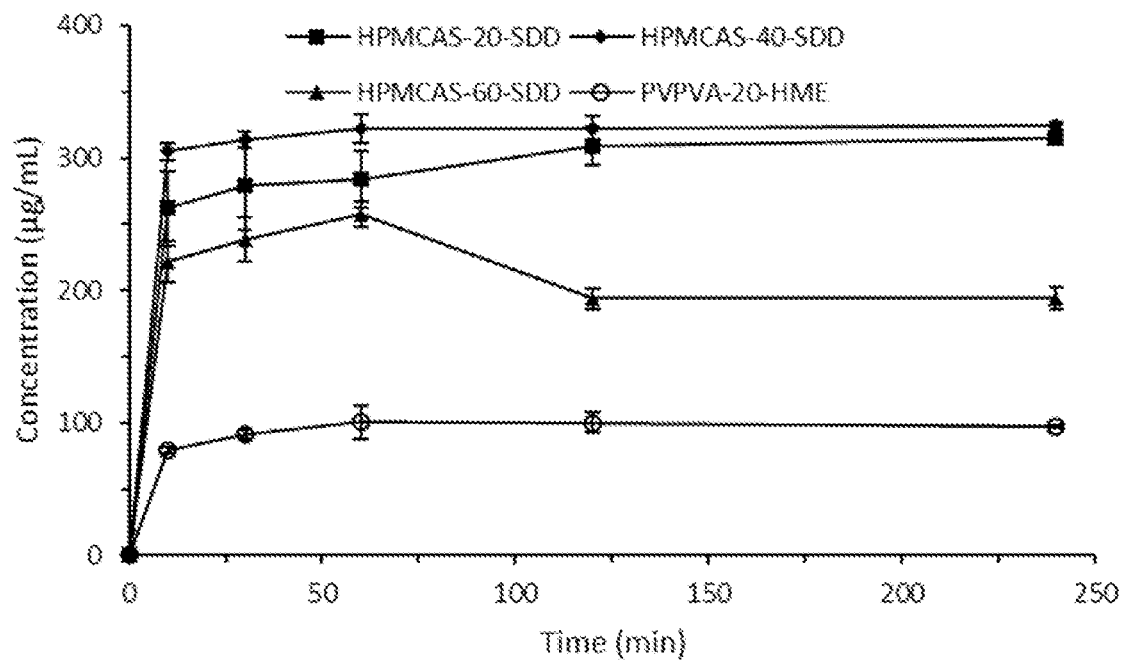
FIG. 3 shows the dissolution behaviors of HPMCAS-20-SDD, HPMCAS-40-SDD, HPMCAS-60-SDD, and PVPVA-20-HME.

Example 7. Dissolution of ASDs with Different Polymers and Different Drug Loading Samples of HPMCAS-20-SDD, HPMCAS-40-SDD, HPMCAS-60-SDD, PVPVA-20-HME were tested for dissolution according to the protocols of Example 5. The results are shown in FIG. 3.

The results show that SDDs with 20% and 40% loading had better dissolution than that with 60% loading. All three SDD had better dissolution than ASD with 20% loading by HME.

Example 8. In Vivo PK

Figure 4:
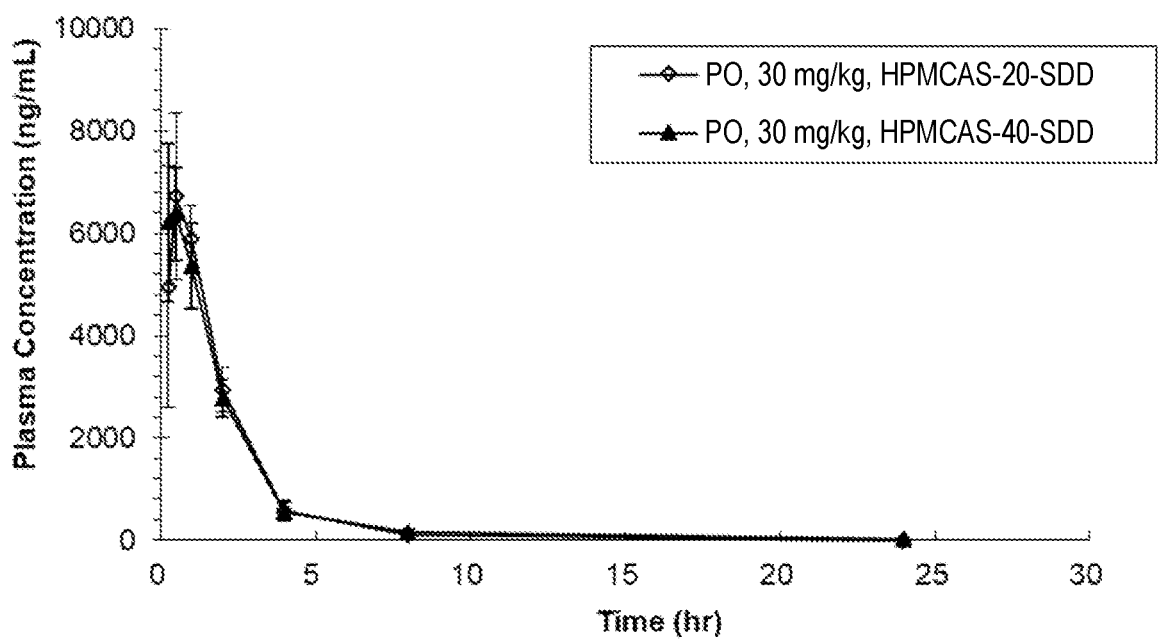
FIG. 4 shows the pharmacokinetics of HPMCAS-20-SDD and HPMCAS-40-SDD following oral administration of 10 mL SDD suspension in 0.5% methylcellulose at a dose of 30 mg/kg in three fed female Sprague Dawley rats.
Figure 5A:
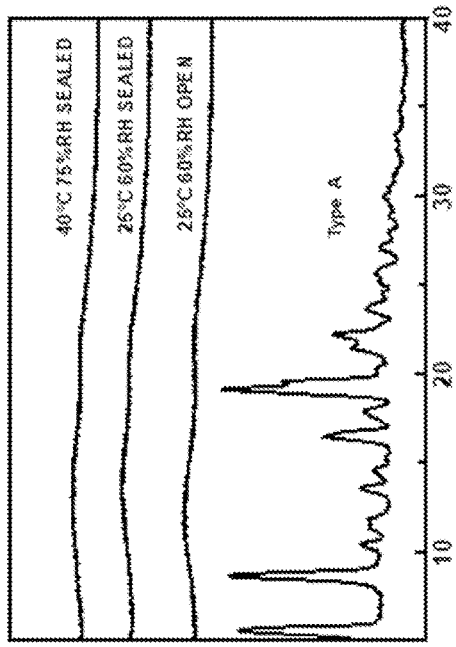
FIGS. 5A-5D show the XRD diagrams of ASD stored at different conditions for one week: (A) PVPVA-20-HME; (B) HMPCAS-20-SDD; (C) HMPCAS-40-SDD; (D) HMPCAS-60-SDD.
Figure 5B:
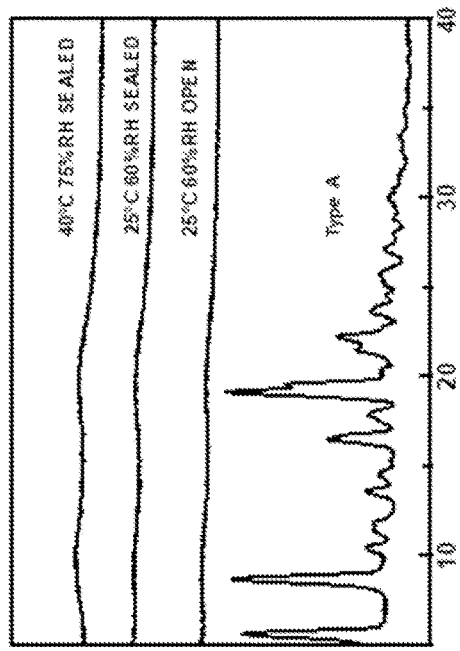
Figure 5C:
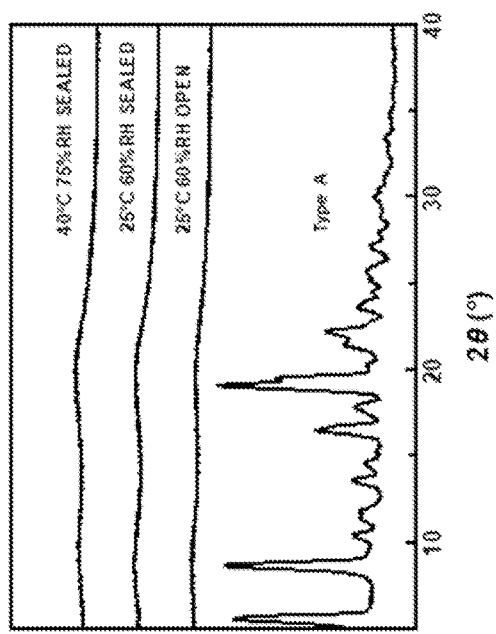
Figure 5D:
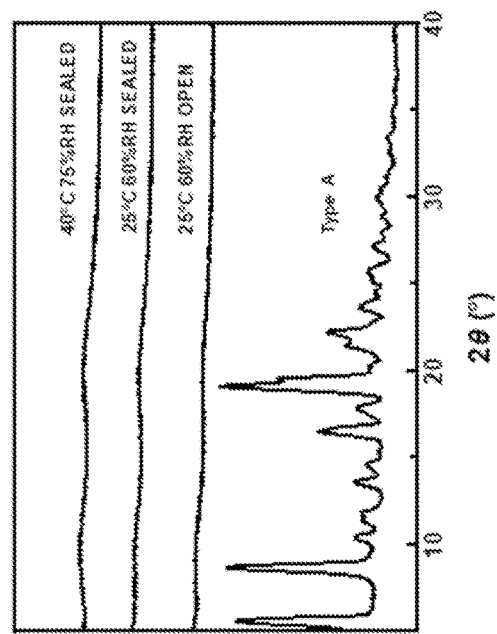

The pharmacokinetics of HPMCAS-20-SDD and HPMCAS-40-SDD samples were evaluated following oral administration (PO) of 10 mL SDD suspension in 0.5% methylcellulose at a dose of 30 mg/kg in three fed female Sprague Dawley rats. Blood samples were collected at 0.25, 0.5, 1, 2, 4, 8 and 24 hours post dose. Concentrations of Compound I were quantified by LC-MS/MS analysis using a API-4500 mass spectrometer. The limit of quantification (LOQ) of the plasma assay was 2 ng/mL. The PK parameters were determined by non-compartmental methods using WinNonlin. The results are summarized in Table 4 and FIG. 4. The results show that SDD with 20% and 40% drug loading had comparable in vivo exposure.

TABLE 4

HPMCAS-20-SDD
PO administration: 30 mg/kg

| Animal (n = 3) | $t_{1/2}$ (hr) | $t_{max}$ (hr) | $C_{max}$ (ng/ml) | $AUC_{last}$ (hr*ng/ml) |
|---|---|---|---|---|
| Mean | 2.63 | 0.500 | 6730 | 15576 |
| SD | 1.06 | 0.000 | 1622 | 2096 |

HPMCAS-40-SDD
PO administration: 30 mg/kg

| Animal (n = 3) | $t_{1/2}$ (hr) | $t_{max}$ (hr) | $C_{max}$ (ng/ml) | $AUC_{last}$ (hr*ng/ml) |
|---|---|---|---|---|
| Mean | 3.26 | 0.417 | 6550 | 16027 |
| SD | 2.23 | 0.144 | 1183 | 2481 |

Example 9. Stability Assessment of ASD

Brown glass vials each containing an ASD sample (A, PVPVA-20-HME; B, HMPCAS-20-SDD; C, HMPCAS-40-SDD; or D, HMPCAS-60-SDD) were placed inside desiccators either open or sealed. Some desiccators contained a saturated potassium bromide solution at the bottom to maintain 60% relative humidity (RH), while others contained a saturated sodium chloride solution at the bottom to maintain 75% relative humidity. The desiccators were then stored in the drying ovens with temperature controlled at either 25° C. or 40° C. After 7-58 days, the samples were evaluated by XRPD, DSC, and dissolution.

XRPD Results

FIG. 5 shows the XRD diagrams of ASD stored at different conditions for one week: (A) PVPVA-20-HME; (B) HMPCAS-20-SDD; (C) HMPCAS-40-SDD; (D) HMPCAS-60-SDD.

The XRPD of Type A crystalline is also shown in FIG. 5. The results show that there was no observed crystalline peak in ASD sample after one-week storage in different conditions, which indicates that all four ASD samples remained as amorphous at least for one week.

DSC Results

The DSC curves of HPMCAS-20-SDD after stored at (A) 25° C. and 60% RH open; (B) 25° C. and 60% RH sealed; and (C) 40° C. and 75% RH sealed for 0-58 days were tested. The results show that only one Tg was observed without extra melting peak, which indicate that ASD remained as amorphous for 58 days under three storage conditions.

The DSC curve of PVPVA-20-HME after stored at (A) 25° C. and 60% RH open, (B) 25° C. and 60% RH sealed, and (C) 40° C. and 75% RH sealed 0-14 days were tested. There is no extra melting peak at different storage conditions for two weeks. Therefore, ASD is relatively stable.

Dissolution Results

Figure 6A:
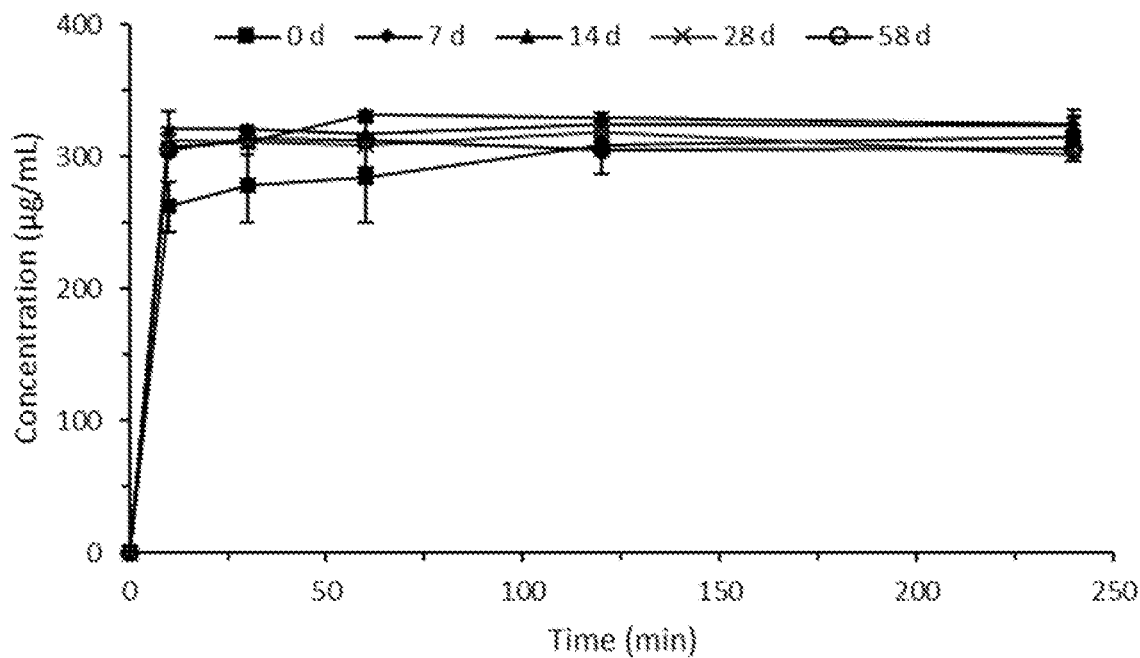
FIGS. 6A-6C show the dissolution profiles of HPMCAS-20-SDD in FaSSIF after the sample was stored at (A) 25° C. and 60% RH open, (B) 25° C. and 60% RH sealed, or (C) 40° C. and 75% RH sealed, for 0-58 days.
Figure 6B:
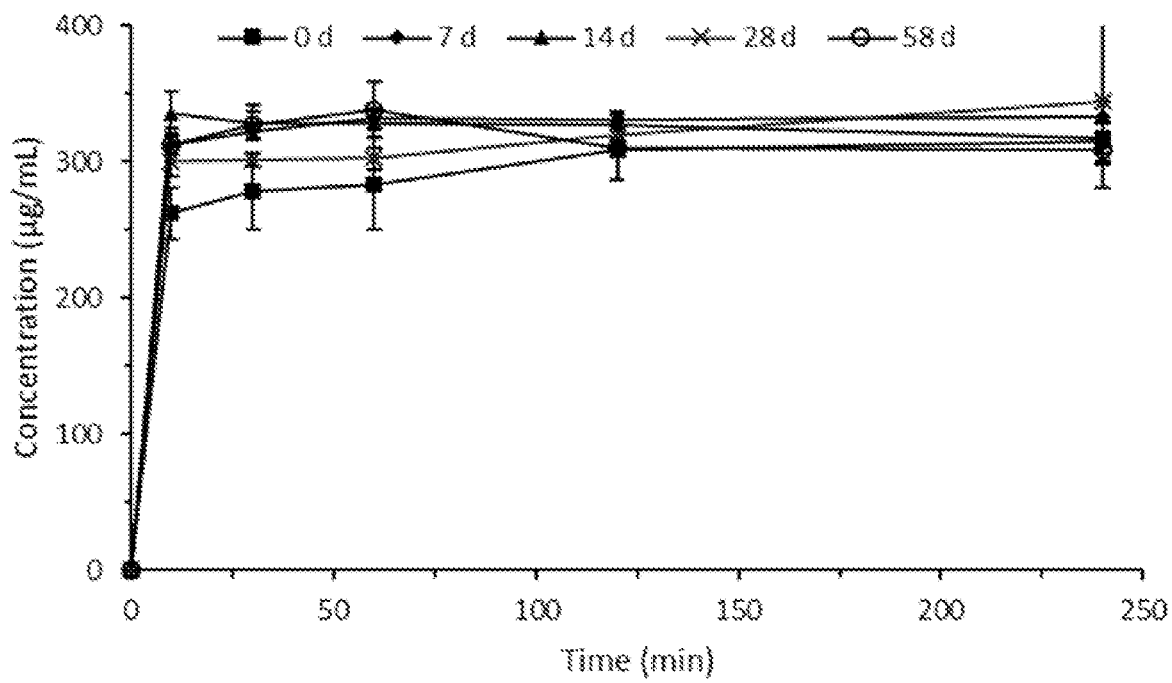
Figure 6C:
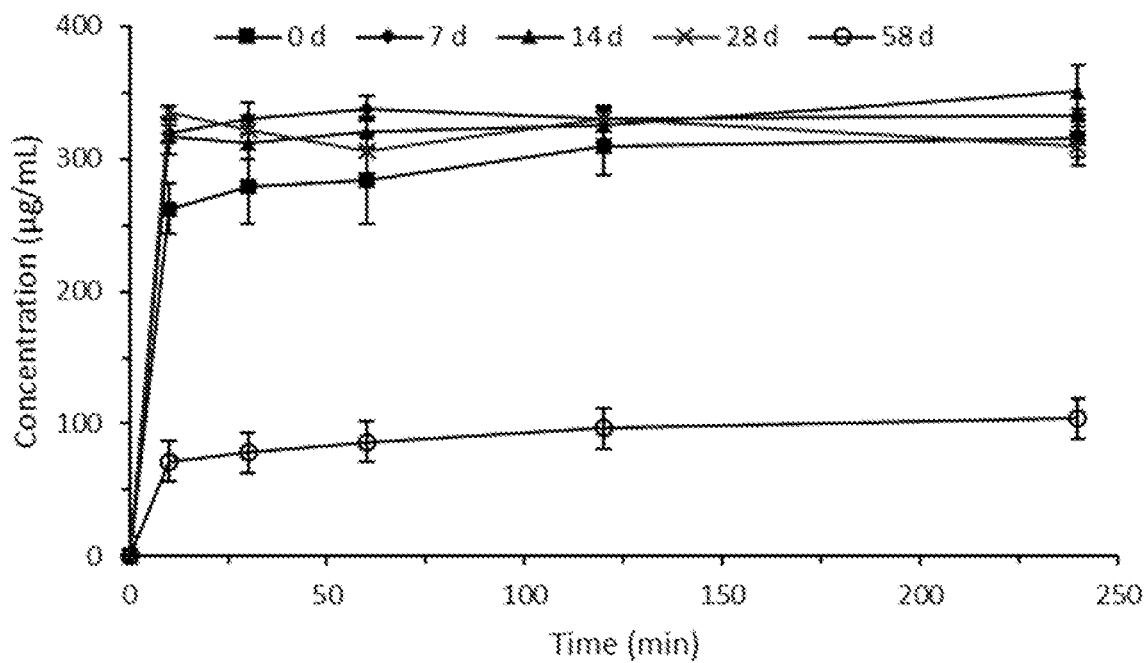

FIG. 6 shows the dissolution profiles of HPMCAS-20-SDD in FaSSIF after the sample was stored at (A) 25° C. and 60% RH open, (B) 25° C. and 60% RH sealed, and (C) 40° C. and 75% RH sealed, for 0-58 days.

The dissolution profiles of HPMCAS-20-SDD in FaSSIF after the sample was stored at (A) 25° C. and 60% RH open, (B) 25° C. and 60% RH sealed, and (C) 40° C. and 75% RH sealed, for different periods of time (0, 7, 14, 28, and 56 days) were tested. The results are summarized in FIG. 6. The results show that there was no dissolution change for ASD after storage at 25° C. and 60% RH for 8 weeks. However, there was signification decrease in dissolution at the storage condition of 40° C. and 75% RH at 8 weeks.

In addition, the dissolution profiles of PVPVA-20-HME in FaSSIF after stored at (A) 25° C. and 60% RH open; (B) 25° C. and 60% RH sealed; and (C) 40° C. and 75% RH sealed, for different periods of time (0, 7, and 14 days) were tested. The results showed that there was no dissolution changed for ASD after storage at 25° C. and 60% RH for 2 weeks.

Example 10. Tablet Formulation

A prototype tablet consisting of HPMCAS-20-SDD and some common excipients, such as microcrystalline cellulose, croscarmellose sodium and sodium stearate as shown in Table 5 was formulated to evaluate the dissolution behavior and stability.

TABLE 5

Examples of Tablet Formulation Containing 100 mg Compound I per Tablet

| Component | Amount per Tablet (mg) |
|---|---|
| HPMCAS-20-SDD | 500 |
| Microcrystalline cellulose | 350 |
| Croscarmellose sodium | 70 |
| Sodium stearate | 1.84 |
| Total | 922 |

Dissolution Assessments

Figure 7:
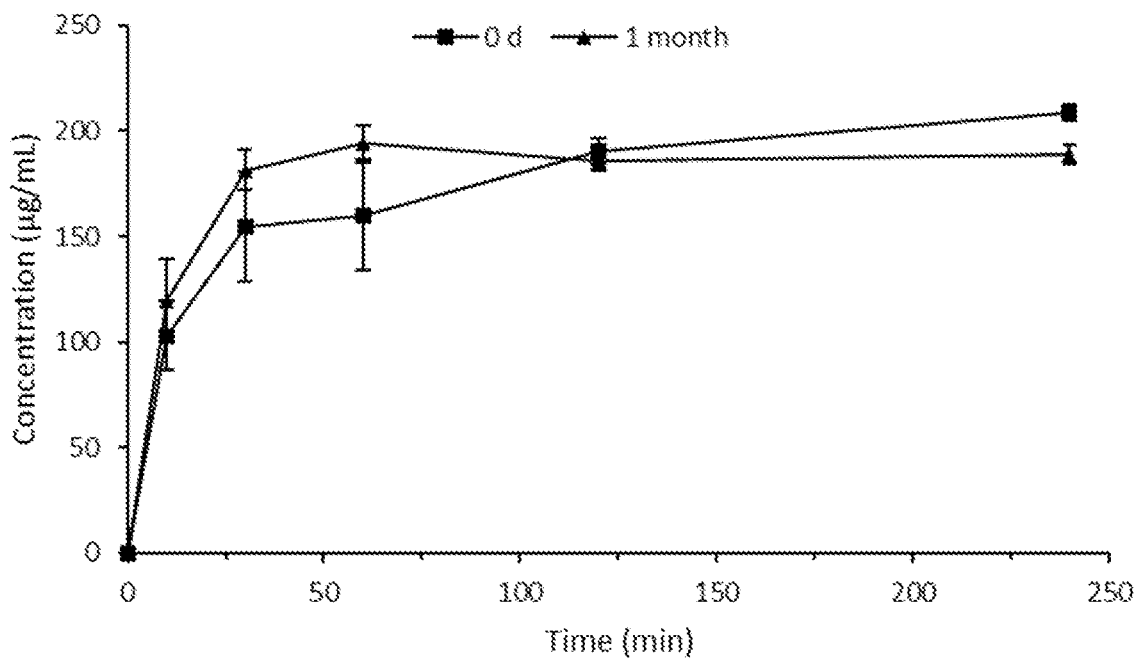
FIG. 7 shows the dissolution behaviors of HPMCAS-20-SDD in a tablet formulation before and after storage under 25° C. and 60% RH for one month.

Sealed brown glass vials containing tablets of Table 5 were placed inside desiccators that had a saturated potassium bromide solution at the bottom to maintain 60% relative humidity (RH) and stored in the drying ovens with temperature controlled at 25° C. After one month, one tablet was added to 500 mL of PBS buffer containing 0.1% Tween 80 at pH 6.5. The mixture was then stirred at 75 rpm at 37° C. At different time intervals (10, 30, 60, 120, 240 min), 2 mL liquid was removed and passed through a 0.45 um filter and the filtrate was analyzed by HPLC. The results (averaged from three repeats) are shown in FIG. 7. After stored under 25° C. and 60% RH for one month, there was no apparent change in the dissolution behavior of the tested tablet.

What is claimed is:

1. An amorphous solid dispersion comprising 20-40% w/w of compound I or a pharmaceutically acceptable salt thereof, and 60-80% w/w of hydroxypropylmethylcellulose-acetate succinate (HPMC-AS),

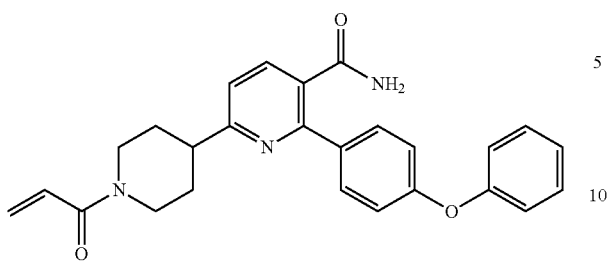

Compound I

2. The amorphous solid dispersion according to claim 1, comprising 20% w/w or 40% w/w of compound I.

3. The amorphous solid dispersion according to claim 1, prepared by spray-drying or hot-melt extrusion.

4. A pharmaceutical composition comprises a pharmaceutically acceptable carrier and a therapeutically effective amount of the amorphous solid dispersion according to claim 1.

5. The pharmaceutical composition of claim 4, in a tablet form or a capsule form.

6. A method for preparing the amorphous solid dispersion of claim 1, comprising the steps:
 (a) dissolving compound I or a pharmaceutically acceptable salt thereof and HPMC-AS in an organic solvent to form a solution, wherein the solution comprises 20-40% w/w of compound I or the pharmaceutically acceptable salt thereof and 60-80% w/w of HPMC-AS; and
 (b) spraying drying the solution to form the amorphous solid dispersion.

* * * * *